United States Patent
Paul et al.

(10) Patent No.: US 10,788,554 B2
(45) Date of Patent: Sep. 29, 2020

(54) METHOD FOR SETTING AN OPERATING PARAMETER OF A MEDICAL DEVICE AND MEDICAL DEVICE

(71) Applicants: Dominik Paul, Bubenreuth (DE); Daniel Nico Splitthoff, Uttenreuth (DE); Thorsten Feiweier, Poxdorf (DE)

(72) Inventors: Dominik Paul, Bubenreuth (DE); Daniel Nico Splitthoff, Uttenreuth (DE); Thorsten Feiweier, Poxdorf (DE)

(73) Assignee: Siemens Healthcare GmbH, Erlangen (DE)

( * ) Notice: Subject to any disclaimer, the term of this patent is extended or adjusted under 35 U.S.C. 154(b) by 303 days.

(21) Appl. No.: 15/901,576

(22) Filed: Feb. 21, 2018

(65) Prior Publication Data
US 2018/0238984 A1    Aug. 23, 2018

(30) Foreign Application Priority Data
Feb. 22, 2017 (DE) .................. 10 2017 202 821

(51) Int. Cl.
*G01R 33/54* (2006.01)
*G01R 33/3875* (2006.01)
(Continued)

(52) U.S. Cl.
CPC ....... *G01R 33/543* (2013.01); *G01R 33/3875* (2013.01); *G01R 33/443* (2013.01); *A61B 5/0037* (2013.01); *A61B 5/055* (2013.01)

(58) Field of Classification Search
CPC .............. G01R 33/543; G01R 33/443; G01R 33/3875; A61B 5/0037; A61B 5/055
(Continued)

(56) References Cited

U.S. PATENT DOCUMENTS 5,339,821 A * 8/1994 Fujimoto ............. A61B 5/0006
128/903
5,836,989 A * 11/1998 Shelton ................ A61N 1/3622
607/27
(Continued)

FOREIGN PATENT DOCUMENTS

DE    102014219780 A1    3/2016

OTHER PUBLICATIONS

German Office Action for German Application No. 102017202821.1, dated Nov. 6, 2017.
(Continued)

*Primary Examiner* — Christopher P McAndrew
(74) *Attorney, Agent, or Firm* — Lempia Summerfield Katz LLC

(57) ABSTRACT

A method for setting an operating parameter of a medical device is provided. The method includes determining a current operating mode of the medical device. A time span available for setting the operating parameter is derived from the determined current operating mode. A setting range of the operating parameter necessary for fulfilling a pre-determined criterion is determined. A setting time necessary for setting the operating parameter according to the determined setting range is determined, and the operating parameter is set according to the setting range, provided the time span available for the setting is at least as long as the necessary setting time.

17 Claims, 1 Drawing Sheet

(51) Int. Cl.
*G01R 33/44* (2006.01)
*A61B 5/055* (2006.01)
*A61B 5/00* (2006.01)

(58) Field of Classification Search
USPC .................................................. 324/309
See application file for complete search history.

(56) References Cited

U.S. PATENT DOCUMENTS

| | | | | |
|---|---|---|---|---|
| 6,801,800 | B2* | 10/2004 | Miyazaki | A61B 5/0263 |
| | | | | 324/306 |
| 7,072,497 | B2* | 7/2006 | Faber | A61B 5/055 |
| | | | | 382/128 |
| 7,590,839 | B2* | 9/2009 | van der Veen | G06F 9/4418 |
| | | | | 713/1 |
| 7,902,821 | B2* | 3/2011 | Nistler | G01R 33/246 |
| | | | | 324/307 |
| RE43,749 | E * | 10/2012 | Miyazaki | A61B 5/7257 |
| | | | | 324/306 |
| 8,298,223 | B2* | 10/2012 | Wham | A61B 18/1206 |
| | | | | 606/32 |
| 9,063,203 | B2* | 6/2015 | Martin | G01R 33/481 |
| 2002/0032376 | A1* | 3/2002 | Miyazaki | A61B 6/541 |
| | | | | 600/410 |
| 2003/0141981 | A1* | 7/2003 | Bui | G06F 19/3462 |
| | | | | 340/608 |
| 2004/0167802 | A1* | 8/2004 | Takada | G06Q 50/22 |
| | | | | 705/2 |
| 2007/0255128 | A1* | 11/2007 | Nistler | G01R 33/246 |
| | | | | 600/410 |
| 2008/0319305 | A1* | 12/2008 | Martin | A61B 6/037 |
| | | | | 600/411 |
| 2010/0095961 | A1* | 4/2010 | Tornesel | A61M 16/209 |
| | | | | 128/203.12 |
| 2016/0091585 | A1 | 3/2016 | Benner et al. | |

OTHER PUBLICATIONS

Van Gelderen, P., et al. "Real-time shimming to compensate for respiration-induced B0 fluctuations." Magnetic Resonance in Medicine 57.2 (2007): 362-368.

Vionnet, L. et. al.: "Full matrix pre-emphasis for higher-order dynamic shimming with 1 kHz bandwidth", in: Proceedings ISMRM, vol. 24; 2016; http://indexsmart.mirasmart.com/ISMRM2016/PDFfiles/1150.html.

* cited by examiner

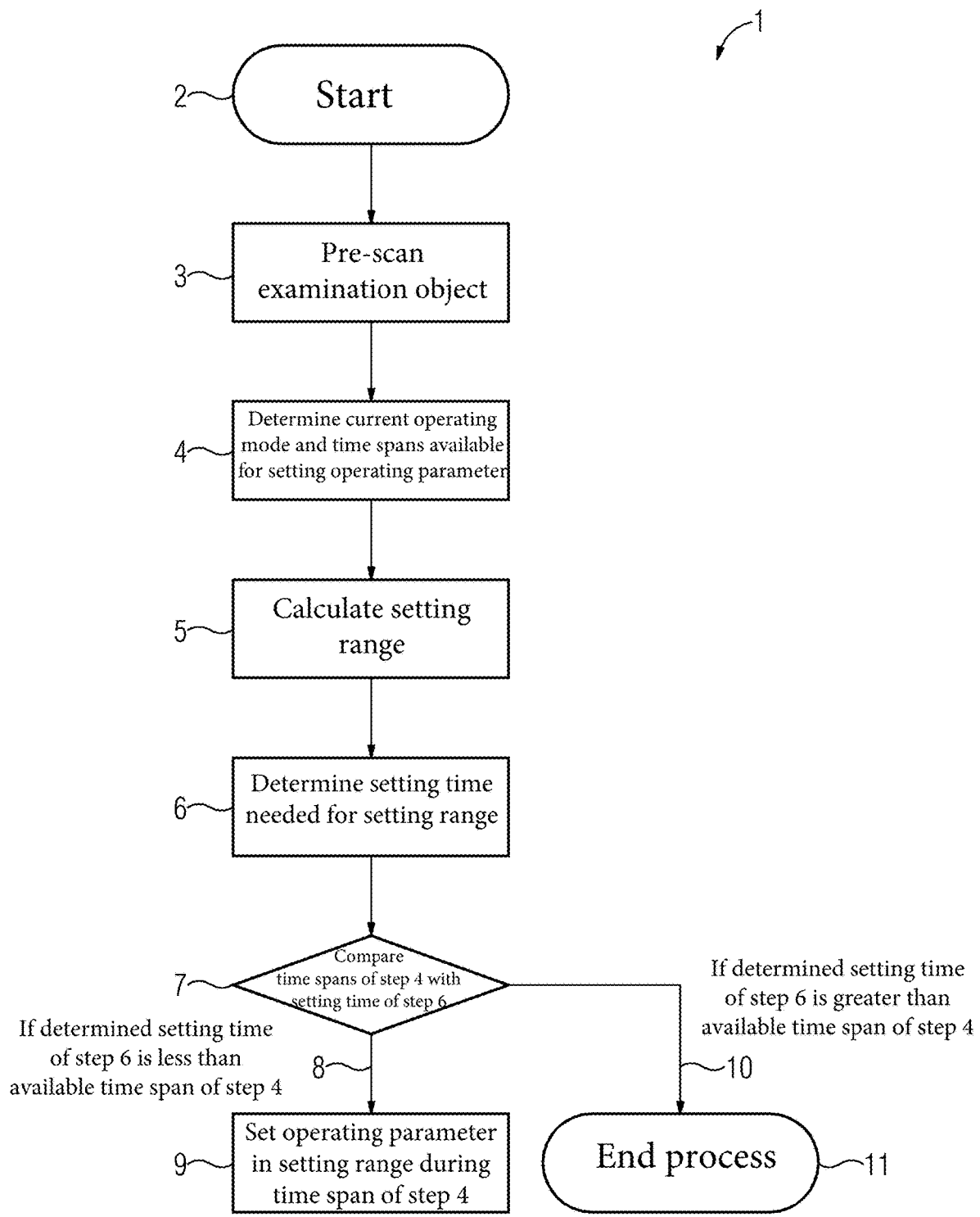

METHOD FOR SETTING AN OPERATING PARAMETER OF A MEDICAL DEVICE AND MEDICAL DEVICE

This application claims the benefit of DE 10 2017 202 821.1, filed on Feb. 22, 2017, which is hereby incorporated by reference in its entirety.

BACKGROUND

The present embodiments relate to setting an operating parameter of a medical device.

It is known that there are operating parameters (e.g., of medical devices), the changing or adjustment of which requires a not negligible timespan. Such relatively slowly settable parameters have conventionally not been changed or not optimally set during a use of the respective device (e.g., during the run-time of a diagnostic examination of an examination object). A sub-optimal result results from this (e.g., an unnecessarily poor image quality if the medical device is an imaging device).

Newer methods attempt to counter this problem, for example, with very extensive and complex pre-scans or through additional, costly device components. In the field of magnetic resonance tomography (MRT, MRI), for example, a setting of an individual magnetic coil may be changed, a response or reaction of the rest of the system resulting therefrom determined, and by a corresponding control of further magnetic coils, a compensation of disadvantageous effects attempted. The coupling calculations and measurements necessary for such a procedure, as well as the settings of individual components may not, however, be carried out on or with conventional MRT devices since for this, extensive changes and adaptations are first to be provided.

SUMMARY AND DESCRIPTION

The scope of the present invention is defined solely by the appended claims and is not affected to any degree by the statements within this summary.

The present embodiments may obviate one or more of the drawbacks or limitations in the related art. For example, an improved automatic situation-adapted operation of a medical device is enabled.

In one embodiment of a method for setting an operating parameter of a medical device, a current operating mode of the device is determined, and therefrom, a time span available for setting the operating parameter is derived. A setting range of the operating parameter necessary for fulfilling a pre-determined criterion is determined. Then, a setting time necessary for setting the operating parameter according to the determined setting range is determined. The operating parameter is set in the specified setting range, provided the time span available for the setting is at least as long as the necessary setting time.

The present embodiments will now be described, for example, with regard to or using the example of MRT or a magnetic resonance tomograph, without restricting the invention to these exemplary cases of use.

The current operating mode or operating type may be pre-determined, for example, by an operating person. Through the specification or selection of the operating mode, a behavior of the medical device may be specified. For example, by the operating mode, a plurality of process steps, operational procedures, and/or operating states that are carried out or performed and/or adopted by the medical device (e.g., one after another in a pre-determined temporal order or sequence) may be determined. The operating mode may therefore be determined, for example, by a plurality of control commands that are, or are to be, carried out, for example, one after another. For example, it may be provided in one operating mode to record a pre-determined number of images at pre-determined time intervals, where a corresponding image recording unit of the device is automatically moved into a respective pre-determined position. Then, for example, the recording of each image, each position adjustment, and/or each provided waiting time between two image recordings and/or position adjustments may be regarded as a respective process step.

On the basis of the operating mode or by an evaluation of the operating mode, it may thus be determined at which time points, respectively, how much time is available to set the operating parameter. These times or time spans may correspond to or include, for example, waiting times or dead times between two individual successive process steps of the medical device. For example, during an examination of a patient in the operating mode, a plurality of successive breath-hold commands temporally spaced from one another (e.g., patient instructions to hold their breath), between which a waiting time of the device is provided to enable the patient to catch breath, may be provided. Due to the inevitably occurring patient movement therein, during this time, no process steps or actions (e.g., no image recordings) are carried out by the device. This time may therefore be used for setting the operating parameter, by which not only may an improved scan result be achieved (e.g., an improved image quality), but also a particularly efficient time usage and therefore a particularly efficient operation of the device. For example, even during operation (e.g., during the running time of the operating mode), those operating parameters that require a relatively long setting time may thus also be set without adapting the operating mode or the device. Effectively, therefore, an improved operation and an improved scan result may be achieved without thereby disadvantageously extending an operating time of the device (e.g., a treatment or examination duration in the respective operating mode).

The criterion that is to be met by setting the operating parameter may be pre-determined or adapted, for example, by the operating person. Therefore, an individual adaptation of the method according to need is thus possible. For example, a limit value or threshold value for a property of the device (e.g., a relative deviation of the operating parameter from another operating parameter or a property of the scan results supplied by the device such as a noise level or a contrast of an image) may be pre-determined as a criterion or for the definition of the criterion.

In order to fulfil this criterion (e.g., not to exceed the pre-determined limit value), the operating parameter is to be set (e.g., particularly adapted, adjusted or changed in value). The respective setting range required (e.g., the size or extent of the necessary adjustment or change of the operating parameter or a value of the operating parameter) may depend on the individual case or the respective individual situation. Thus, even with the same operating mode (e.g., for different examination objects), different setting ranges may be necessary to meet the criterion. In other words, therefore, the required setting range for meeting the pre-determined criterion may be dependent on the current examination object.

The setting time required for setting the operating parameter according to the specified setting range is the time span that is to be provided with a proper operation of the device in order by corresponding control of the device to change the actual value of the operating parameter from a starting value to a target value. The starting value and the target value differ from one another precisely by the setting range. The necessary setting time may also include an adaptation time of the device or of some or all of the components of the device and/or of the examination object or of an interaction or reciprocity between the device and the examination object. In other words, the necessary setting time may include, for example, a settling time of the device and/or of the overall system consisting of the device and the examination object, during which a corresponding stable state becomes established.

The necessary setting time may depend, for example, on the setting range since, for example, for a coarser setting range, a longer setting time may be required. The setting time may also depend on the respective operating parameter, since different operating parameters may possibly be set or changed with different rapidity. Apart from technical limitations for a maximum possible adjustment or setting speed of the value of the operating parameter, alternatively or additionally, a maximum change or setting speed or rate may be stipulated. By this, for example, a change speed of a magnetic field in a volume, for example, of the respective examination object may be restricted in order to prevent undesirable influences or effects.

In order to determine the necessary setting time, for example, a characteristic map may be stored in a storage apparatus of the medical device or of a control device.

Once the time span available for setting the operating parameter has been derived or determined and the necessary setting time has also been determined, these two time spans are compared with one another. This comparison may also be carried out, for example, by the control device or an evaluating device.

The operating parameter and/or the value of the operating parameter is set, for example, also by the control device, according to the specified setting range if the time span available for this is exactly as long as or longer than the setting time necessary therefor.

The individual method steps may be carried out, automated, by the control device or another control device. The control device may wholly or partially include the sensors, evaluating and/or calculating devices necessary for carrying out the method, or may be connected thereto via corresponding data connections. The control device and/or the possibly present devices may be part of the medical device. The control device and/or the possible present devices may also, however, be separate from the medical device.

By the use, enabled in this way, of available time spans or time periods for setting the operating parameter, an improvement of conventional operating methods of medical devices may be achieved without a significant effort therefor or even a respective new medical device with additional equipment being needed. Even if, in the context of the method of one or more of the present embodiments, in an actual application, it arises that the time span needed for setting the operating parameter is smaller than the necessary setting time, with the present method, at least no worsening of respective scan results is caused. It may also be possible that in an actual application, a plurality of mutually separate or independent time spans are available for setting the operating parameter, where possibly only one or some of these time spans actually suffice for setting the operating parameter or a corresponding value in the respectively determined setting range (e.g., are long enough for this). Even in such a case, however, through the present method, an advantage is achieved with at least point-wise improvement of some results.

The operating parameter may be set, for example, in a particular available time span, in each case, for the next process step following this time span. Since the setting range may be different, depending on a current value of the operating parameter and the respective process step, different setting times may be needed before or for different process steps.

For the purpose of the present embodiments, the setting of the operating parameter may be the setting of the value of the operating parameter as gathered from the respective context. For example, the setting of the operating parameter is therefore not to be interpreted in the sense of a selection or stipulation of one particular of a plurality of operating parameters.

In one embodiment, a pre-scan is carried out, the scan result of which is used for determining the necessary setting range. The pre-scan may be carried out, for example, with the medical device. Using the pre-scan, the respective examination object may be examined or scanned completely or partially before a detailed main examination of the examination object in order to gather data on the examination object that is necessary or useful for the main examination. The main examination may include the stated process steps or the sequence of process steps. For example, the pre-scan is carried out without setting the operating parameter, where the operating parameter may be left, for example, on a pre-determined standard value for the pre-scan. The data gathered by the pre-scan (e.g., the scan result or results of the pre-scan) may be used to determine the necessary setting range of the operating parameter and/or, for example, may enable a simpler and/or improved determination of the setting range. The pre-scan may be carried out possibly faster, more easily, and with less effort than the main scan and contribute to an improved result of the main scan. The main examination may be the examination or another examination of the examination object in which the operating parameter is set according to the method of one or more of the present embodiments. The pre-scan may be tuned to the operating parameter to be set, providing that the pre-scan is adjusted thereto. Thus, in the context of the pre-scan, for example, the scan data that is relevant for the operating parameter (e.g., for setting the operating parameter) is detected. For example, using the pre-scan, an influence of the examination object on a magnetic field generated by the medical device (e.g., distribution, homogeneity and/or local shape) may be detected.

In one embodiment, a pre-determined sequence of process steps of the current operating mode is evaluated. In order to derive the time span available for setting the operating parameter, an execution time of each of such process steps that are insensitive to the setting of the operating parameter is then also taken into account. The respective execution time of the process steps may not provide only an execution time point, but, for example, a time span provided or needed for the implementation or execution of the respective process step. In other words, the operating parameter may thus be set (e.g., a corresponding value set or changed), while the medical device carries out a process step which is insensitive to this setting process. A process step is, for example, insensitive to the setting of the operating parameter if an execution and/or a result of the process step is not influenced by the setting. As a result, not only waiting or dead times, but also process or activity times of the device may be used for setting the operating parameter. This has the advantage that overall, more time is available (e.g., may be used for setting the operating parameter). By this, an improved scan result (e.g., an improved image quality) may be achieved in general and/or in more different situations.

The evaluation of the pre-determined sequence of process steps may include, for example, a classification of the individual process steps with regard to sensitivity in relation to the setting (e.g., changing) of the operating parameter. This classifying or classification may be dependent on the operating parameter (e.g., on which operating parameter is or is to be set). A limit sensitivity may be pre-determined. Based on this, the different process steps are classified into process steps that are sensitive and not sensitive or insensitive to the setting of the operating parameter. In order to be able to carry out the classification as simply as possible, for example, respective sensitivities of different process steps are stored with respect to the setting of the one or more operating parameters (e.g., in a table) in a storage device that is or may be accessed during the method of one or more of the present embodiments.

In one embodiment, a "shim term" of at least the second order of a magnetic field is set as the operating parameter. In other words, therefore, a non-linear component of the magnetic field generated by the medical device is set. This is an advantageous application case of the present embodiments since such shim terms of higher order typically need more setting time than is provided or allocated in conventional operating methods of medical devices for the setting of operating parameters. At the same time, by the setting ("shimming" or "shim adaptation") of such terms or magnetic field components, a significant improvement of respective scan results as compared with conventional methods may be achieved.

In one embodiment, a pre-determined limit value of a spatial homogeneity of a magnetic field generated or created by the medical device (e.g., in an examination object) is used as the criterion to be fulfilled. In other words, the examination object is thus permeated by the magnetic field, where inhomogeneities of the magnetic field may arise through an influence of the examination object on the magnetic field. Such inhomogeneities of the magnetic field (e.g., of a spatial distribution of the magnetic field) may lead to local frequency deviations (e.g., in MRT). In this way, for example, a saturation behavior may be disadvantageously influenced. A magnetic field that is homogeneous also in the volume of the examination object is advantageous since then a better image quality may be achieved in image recordings of the examination object.

Through the setting of the operating parameter, inhomogeneities of the magnetic field (e.g., in the region or volume of the examination object) may be evened out (e.g., compensated). The pre-determined limit value of the spatial homogeneity may define a deviation of the field or the field distribution from a homogeneous state or from a homogeneous magnetic field or a homogeneous magnetic field distribution. In other words, by the limit value, a measure for a maximum inhomogeneity of the magnetic field or the magnetic field distribution is therefore pre-determined. The corresponding criterion may therefore be considered as fulfilled if the inhomogeneity (e.g., the deviation from a perfect homogeneity) is less than the limit value. Since the achievement of perfect homogeneity is normally not practicable, by the limit value, a quality of the respective scan results may be set or adjusted as needed. A higher limit value enables greater deviations (e.g., greater inhomogeneities), by which the necessary setting range of the operating parameter for fulfilling the criterion may be restricted.

In one embodiment, the limit value is specified automatically dependent upon the derived available time span for setting the operating parameter. In this way, the quality of the scan results may be automatically optimized. A plurality of different limit values may be defined or stipulated for different operating modes and/or for different process steps or available time spans. By this, the quality of the scan results may be further improved (e.g., specifically in particular examination areas or regions of the examination object).

In one embodiment, the medical device is an imaging device, and the operating parameter is set once and used for a plurality of, successive image recordings (e.g., successive image recordings). In other words, the medical device is thus used for generating images of the examination object, where for a plurality of image recordings in each case, the same value of the operating parameter is used. The operating parameter is therefore not set for each individual image recording separately, but only once for a group of image recordings. The value of the operating parameter may be set, for example, to an optimum value (e.g., a mean value by which the best average image quality of all image recordings of the group is achieved). Such a value may be determined, for example, by a pre-scan and corresponding evaluations. By this embodiment of the method, at least on average, a quality even of those image recordings, immediately before the recording of which insufficient setting time was available for setting the operating parameter, may also be improved.

Additionally or alternatively to setting or specifying the operating parameter or a corresponding value for the image recordings, the operating parameter or the corresponding value may be set for or in relation to a particular subregion of the examination object. In other words, the operating parameter may be set such that the pre-determined criterion is fulfilled in at least the subregion of the examination object. By this, for example, a particular subregion (e.g., region of interest (ROI)) of the examination object that is to be imaged with the best possible image quality may be pre-determined. In conventional methods, it is known in a similar connection to define optimization regions (e.g., "cuboids") that may each correspond, for example, to a "slice" of the examination object. For example, in breath-hold scans, a plurality of such adjacent slices may be grouped together into packets (e.g., "slice packets" or "concats"). In such a case, with the present embodiments, the operating parameter for the overall packet may be set, so that for all the slices or slice images of the respective packet, the same set value of the operating parameter is used. For such packets or groups of slices or optimization regions that include a plurality of slices, the expression "cuboid groups" may be used. Typical slices (e.g., cuboids) may have, for example, a width and height of respectively 19 or 22 cm and a thickness of 0.3 to 0.5 mm up to some centimeters.

In one embodiment, in addition to the operating parameter set for the plurality of image recordings or for the subregion, at least one second operating parameter may be separately set and used for each of the image recordings. This second operating parameter may be, for example, more quickly settable (e.g., requiring less setting time), so that for each individual image recording or for each individual slice, the second operating parameter may be set and/or used independently. In other words, the medical device may thus have a plurality of settable operating parameters of which a subset is set separately and individually for each process step (e.g., therefore, for each image recording or for each slice and of which another subset is set once together for a group of process steps or for a cuboid group; for a plurality of successive image recordings or for all recordings of a particular subregion of the examination object), and is then used with the same set value. In one embodiment, the second operating parameter is set for each of the image recordings taking account of or depending upon the value of the operating parameter set for the respective image recording. The relatively rapidly settable second operating parameter or parameters may therefore be set dependent upon the value of the relatively slowly settable operating parameter. A non-linear magnetic field shim term of at least the second order may be set as an operating parameter, and a corresponding linear shim term may be set as a second operating parameter. Respective basis functions (e.g., spherical harmonic functions) are non-orthogonal to one another. The different operating parameters may therefore generate different magnetic fields or magnetic field components within a cuboid due to their different orders or gradients.

An storage medium (e.g., a non-transitory computer-readable storage medium) of one or more of the present embodiments includes or contains a program code configured, on execution by a processor device of a control device (e.g., a control device of a medical device), to carry out the method.

A medical device of one or more of the present embodiments includes a control device configured to access a storage medium and to carry out the program code stored thereon. The storage medium may be part of the control device or part of the medical device. The storage medium may, however, be separate from the medical device, where the control device may then access the storage medium, for example, via a corresponding data connection.

In one embodiment, the medical device may include or be a magnetic resonance tomograph.

The properties and developments of the method, the storage medium, and the medical device and also the corresponding advantages set out above and in the following are each analogously and reciprocally transferrable between the method, the storage medium, and the medical device. This applies also for components and apparatus used or usable for the execution of the method. Accordingly, in the present case, a respective explicit formulation of each aspect of the present embodiments is dispensed with both for the method and also for the storage medium and the medical device.

BRIEF DESCRIPTION OF THE DRAWINGS

FIG. 1 shows a schematic flow diagram of one embodiment of a method for setting an operating parameter of a medical device.

DETAILED DESCRIPTION

Components of the individual embodiments as described are each individual features and are also to be considered independently of one another. Each also further develops the present embodiments independently of one another and are thus also to be considered individually, or in a different combination from that shown, as a constituent of the present embodiments. The embodiments described are also enhanceable through other of the previously described features of the present embodiments.

FIG. 1 shows, by way of example, a schematic flow diagram 1 of a method for setting an operating parameter of a medical device. In the present case, the medical device may be a magnetic resonance tomograph. The method begins with a start 2, at which, for example, the medical device is put into operation. An operating mode of the device may also be set or pre-determined in that, for example, a particular operating mode is selected and/or a sequence of individual process steps or operational procedures or corresponding control commands are specified. Examples for this may include preparatory scans of an examination object, dummy scans, positioning or navigator processes, breath-hold commands, image recordings, and the like.

Subsequently, a pre-scan 3 is carried out in which the examination object is entirely or partially scanned to acquire basis data usable in subsequent method steps. The pre-scan 3 may be carried out, for example, at increased speed and/or with reduced effort in relation to a later main examination.

In the present example, following the pre-scan 3, a determination and evaluation 4 of the current or pre-determined operating mode is automatically carried out by the medical device independently. Alternatively, this determination and evaluation 4 of the operating mode may be carried out entirely or partially before the pre-scan 3 or in parallel with the pre-scan 3. In the context of the evaluation 4, for example, the sequence of process steps provided in the current operating mode is analyzed in order to determine times, time periods, or time spans that are available for setting the operating parameter. Here, a classification of the individual process steps may be carried out with regard to sensitivity in relation to the setting of the operating parameter.

Time spans that may be assessed as available for setting the operating parameter may be, for example, waiting or dead times between two process steps and/or execution times of process steps that are insensitive to the setting. Such insensitive process steps may be, for example, times linked to one or more breath-hold commands that are afforded to a patient serving as the examination object, for catching breath. Equally, however, additionally or alternatively, other temporal portions of the sequence of process steps and possibly pauses are not or are only negligibly sensitive to the setting of the operating parameter of the medical device that are then therefore also assessed or included as available for setting. This may concern, for example, process steps that do not contribute immediately and directly to an output signal or scan result of the medical device (e.g., dummy scans).

Based on the basis data acquired by or during the pre-scan 3, a calculation 5 of a necessary setting range of the operating parameter is carried out. The necessary setting range results, for example, firstly from the influence or a property of the examination object, whereby, for example, a magnetic field generated by the medical device and permeating the examination object is locally distorted or changed (e.g., disrupted in homogeneity), and secondly from a pre-determined criterion that is to be fulfilled.

As operating parameters, a shim term of at least the second order of the magnetic field may be used (e.g., set). With a suitable setting of the operating parameter, therefore, the magnetic field may be influenced in order to compensate for inhomogeneities. In place of the magnetic field component itself, for example, a current or a current strength that generates the magnetic field or the magnetic field component of at least second order may be used as the operating parameter. Equally, for example, an eddy current compensation may serve or be used as the operating parameter, where the respective corresponding pre-determined criterion may be fulfilled directly by setting corresponding currents or fields as the operating parameter. In this case, the criterion to be fulfilled may be, for example, that a current strength of an eddy current (e.g., in a magnetic coil of the magnetic resonance tomograph) is lower than a pre-determined limit current value.

If the necessary setting range is known through the calculation 5, a determination 6 of the setting time necessary for realizing this setting range is performed. This determination 6 may be or include a calculation and/or an estimate. In the determination 6 of the necessary setting time, for example, specific properties of the respective medical device, an absolute value of the operating parameter to be set, and/or other stipulations such as, for example, a pre-determined maximum speed or rate of change of a current, of a magnetic field, and/or of an electric field may be taken into account.

Subsequently, in a comparison 7, the time span for setting derived or determined from the evaluation 4 is compared with the required setting time determined through the determination 6. If the required setting time is smaller or shorter than or equal to the time span available for setting, then the method follows a path 8 for operating parameter setting 9. In other words, the operating parameter is therefore changed according to the calculated setting range. This operating parameter setting 9 is then carried out during the time span determined by the evaluation 4.

If the comparison 7 reveals that the required setting time is greater than the time span available for setting, then the method follows a path 10 to a process end 11.

The method or a variation thereof described here may be carried out in parallel or sequentially for a plurality of different operating parameters. For example, the process steps identified with the reference signs 4 to 8 can be carried out before or during the examination of the examination object.

Overall, with the method for setting the operating parameter of the medical device with particularly little effort, an improved automatic situation-adapted operation of the medical device may be enabled in order, for example, to generate improved scan results (e.g., images with better sharpness, resolution, and/or a better signal-to-noise ratio).

Magnetic resonance tomography is a particularly relevant example for a field of application of the method described. In magnetic resonance tomography, for example, fat saturation techniques (e.g., "chemical shift selective saturation," "water excitation," "spectral attenuation inversion recovery") that react sensitively to local frequency deviations through inhomogeneous spatial distributions of a static magnetic field are used. In areas or regions of such magnetic field inhomogeneities, the fat saturation may be impaired. This is due thereto that for fat saturation, frequency-selective pulses that affect the entire examination volume are used. This problem increases with rising magnetic field strength. Conventional solution approaches for compensation of the inhomogeneities take account only of linear shim terms, since the field homogeneity dynamically adapts during operation of the magnetic resonance tomograph (e.g., changes during the examination of the examination object) and it was conventionally assumed that during the run time of the examination, due to the setting times required, only particularly rapidly settable parameters (e.g., the linear shim terms) may be set dynamically. Shim terms of second or higher order are therefore not adapted or set during conventional methods, since these may require longer setting times. These longer setting times may be pre-determined or caused (e.g., through eddy currents and their effects occurring during the setting) through switching times of devices or components (e.g., an amplifier) and/or through physiological effects in the examination object, since possible rates of change of the value of the operating parameter may be restricted or limited thereby. In conventional methods, therefore, only such operating parameters are set dynamically during the running time that require, for example, setting times of less than 5 ms. With the method described above, however, such operating parameters that, for example, require setting times of more than 5 ms, more than 50 ms, or, for example, one or more seconds may be set.

The elements and features recited in the appended claims may be combined in different ways to produce new claims that likewise fall within the scope of the present invention. Thus, whereas the dependent claims appended below depend from only a single independent or dependent claim, it is to be understood that these dependent claims may, alternatively, be made to depend in the alternative from any preceding or following claim, whether independent or dependent. Such new combinations are to be understood as forming a part of the present specification.

While the present invention has been described above by reference to various embodiments, it should be understood that many changes and modifications can be made to the described embodiments. It is therefore intended that the foregoing description be regarded as illustrative rather than limiting, and that it be understood that all equivalents and/or combinations of embodiments are intended to be included in this description.

The invention claimed is:

1. A method for setting an operating parameter of a medical device, the method comprising:
    determining a current operating mode of the medical device;
    deriving a time span available for setting the operating parameter from the determined current operating mode;
    determining a setting range of the operating parameter necessary for fulfilling a pre-determined criterion, the setting range being a range of values between a starting value of the operating parameter and a target value of the pre-determined criterion;
    determining a setting time necessary for setting the operating parameter according to the determined setting range, the setting time being a time necessary to change a value of the operating parameter from the starting value to the target value; and
    setting the operating parameter in the determined setting range when the derived time span available for the setting is at least as long as the determined setting time.

2. The method of claim 1, further comprising carrying out a pre-scan,
    wherein determining the necessary setting range comprises determining the necessary setting range using a scan result of the carried out pre-scan.

3. The method of claim 1, further comprising evaluating a pre-determined sequence of process steps of the current operating mode,
    wherein determining the time span available comprises determining the time span available taking into account an execution time of each of the pre-determined sequence of process steps that are insensitive to the setting of the operating parameter.

4. The method of claim 1, wherein setting the operating parameter comprises setting a shim term of at least a second order of a magnetic field as the operating parameter.

5. The method of claim 1, wherein the pre-determined criterion to be fulfilled includes a pre-determined limit value of a spatial homogeneity of a magnetic field.

6. The method of claim 5, wherein the pre-determined limit value of the spatial homogeneity of the magnetic field is in an examination object.

7. The method of claim 1, wherein the medical device is an imaging device, and the operating parameter is set once and used for a plurality of image recordings.

8. The method of claim 7, wherein the plurality of image recordings are successive image recordings.

9. The method of claim 8, further comprising separately setting and using at least one second operating parameter for each of the image recordings.

10. In a non-transitory computer-readable storage medium storing instructions executable by one or more processors to set an operating parameter of a medical device, the instructions comprising:
   determining a current operating mode of the medical device;
   deriving a time span available for setting the operating parameter from the determined current operating mode;
   determining a setting range of the operating parameter necessary for fulfilling a pre-determined criterion, the setting range being a range of values between a starting value of the operating parameter and a target value of the pre-determined criterion;
   determining a setting time necessary for setting the operating parameter according to the determined setting range, the setting time being a time necessary to change a value of the operating parameter from the starting value to the target value; and
   setting the operating parameter in the determined setting range when the derived time span available for the setting is at least as long as the determined setting time.

11. The non-transitory computer-readable storage medium of claim 10, wherein the instructions further comprise carrying out a pre-scan,
   wherein determining the necessary setting range comprises determining the necessary setting range using a scan result of the carried out pre-scan.

12. The non-transitory computer-readable storage medium of claim 10, wherein the instructions further comprise evaluating a pre-determined sequence of process steps of the current operating mode,
   wherein determining the time span available comprises determining the time span available taking into account an execution time of each of the pre-determined sequence of process steps that are insensitive to the setting of the operating parameter.

13. The non-transitory computer-readable storage medium of claim 10, wherein setting the operating parameter comprises setting a shim term of at least a second order of a magnetic field as the operating parameter.

14. The non-transitory computer-readable storage medium of claim 10, wherein the pre-determined criterion to be fulfilled includes a pre-determined limit value of a spatial homogeneity of a magnetic field.

15. The non-transitory computer-readable storage medium of claim 14, wherein the pre-determined limit value of the spatial homogeneity of the magnetic field is in an examination object.

16. A medical device comprising:
   a controller configured to access a non-transitory computer-readable storage medium storing instructions and execute the instructions to:
      determine a current operating mode of the medical device;
      derive a time span available for setting the operating parameter from the determined current operating mode;
      determine a setting range of the operating parameter necessary for fulfilling a pre-determined criterion, the setting range being a range of values between a starting value of the operating parameter and a target value of the pre-determined criterion;
      determine a setting time necessary for setting the operating parameter according to the determined setting range, the setting time being a time necessary to change a value of the operating parameter from the starting value to the target value; and
      setting the operating parameter in the determined setting range when the derived time span available for the setting is at least as long as the necessary setting time.

17. The medical device of claim 16, wherein the medical device comprises a magnetic resonance tomograph.

* * * * *